United States Patent [19]

Knudsen et al.

[11] Patent Number: 4,482,640

[45] Date of Patent: Nov. 13, 1984

[54] ETHYLENE OLIGOMERIZATION

[75] Inventors: Ronald D. Knudsen; Stephen E. Reiter, both of Bartlesville, Okla.

[73] Assignee: Phillips Petroleum Company, Bartlesville, Okla.

[21] Appl. No.: 490,596

[22] Filed: May 2, 1983

[51] Int. Cl.³ .............................................. B01J 31/04
[52] U.S. Cl. ..................................... 502/155; 502/161; 502/162; 585/523; 585/527
[58] Field of Search ........................ 502/155, 161, 162

[56] References Cited

U.S. PATENT DOCUMENTS

| | | | |
|---|---|---|---|
| 3,366,704 | 1/1968 | Stapp | 260/683.15 |
| 3,424,816 | 1/1969 | McClure et al. | 260/683.15 |
| 3,535,397 | 10/1970 | Schott | 502/155 X |
| 3,644,563 | 2/1972 | Bauer et al. | 260/683.15 |
| 3,644,564 | 2/1972 | Zwet et al. | 260/683.15 |
| 3,647,906 | 3/1972 | Farley | 260/683 |
| 3,647,914 | 3/1972 | Glockner et al. | 260/683.15 |
| 3,647,915 | 3/1972 | Bauer et al. | 260/683.15 |
| 3,661,803 | 5/1972 | Bauer et al. | 502/155 |
| 3,676,523 | 7/1972 | Mason | 260/683.15 |
| 3,686,159 | 8/1972 | Bauer et al. | 260/94.9 |
| 3,686,351 | 8/1972 | Mason | 260/683.15 |
| 3,726,938 | 4/1973 | Berger | 260/683 |
| 3,737,475 | 6/1973 | Mason | 260/683.15 |
| 3,808,246 | 4/1974 | Fahey | 502/155 X |
| 3,825,615 | 7/1974 | Lutz | 260/683.15 |
| 3,907,923 | 9/1975 | Yoo | 260/683.15 |

*Primary Examiner*—Patrick Garvin

[57] ABSTRACT

A novel ethylene oligomerization catalyst is provided consisting essentially of a nickel compound, a phosphine compound, and an acid. In addition, an improved ethylene oligomerization process is provided which comprises contacting ethylene with the novel catalyst composition present, in an effective solvent, at a temperature from about 0° C. to about 200° C. As a result of the inventive process, high catalyst productivity and good selectivity to desired oligomeric products are obtained.

12 Claims, No Drawings

ETHYLENE OLIGOMERIZATION

This invention relates to a novel catalyst for the oligomerization of ethylene. This invention also relates to a novel process for the oligomerization of ethylene.

A variety of catalysts, both homogeneous and heterogeneous, have been utilized to convert ethylene into olefinic products of higher molecular weight, i.e. to dimer and trimer as well as higher oligomers. For example U.S. Pat. No. 3,647,915 discloses a process for the oligomerization of ethylene employing a catalyst comprising an atom of nickel chelated with a chelating ligand having a tertiary organophosphine moiety and a carbonyl ligand. The rather complex chemical nature of the chelating ligand in U.S. Pat. No. 3,647,915 renders the use of the catalyst disclosed therein relatively expensive.

U.S. Pat. No. 3,644,564 discloses the oligomerization of ethylene in the presence of a catalyst comprising nickel(O) complexed with fluorine containing ligands.

While the catalyst systems disclosed by the above references are operable for the oligomerization of ethylene, they are merely typical of other oligomerization catalysts known in the art. By using these and other known catalyst systems for the oligomerization of ethylene, one has not always achieved high productivity of the catalyst, good selectivity to a desired oligomeric product or a combination of both.

Because of the increasing importance that oligomers are playing in the chemical industry, as exemplified by the importance of α-olefins, processes which make even slight improvements in the availability of desired oligomers over existing processes are highly desirable.

Therefore, it is an object of this invention to provide an improved catalyst for the oligomerization of ethylene which is a common building block for oligomers such as higher α-olefins. A further object of this invention is to provide an improved process for the oligomerization of ethylene.

Other aspects, objects and advantages of the present invention will become apparent from a study of this specification and the claims.

In accordance with one embodiment of the present invention, we have discovered a novel catalyst composition for the oligomerization of ethylene which is highly productive and affords good selectivity to desired oligomers. This improved catalyst composition consists essentially of:

(a) at least one nickel compound selected from the group consisting of: bis(1,5-cyclooctadiene)nickel(O), bis(tricyclohexylphosphine)nickel(O), nickel tetracarbonyl, (cyclododecatriene)nickel, and bis(ethylene)(dicyclohexylphosphine)nickel;

(b) a phosphine compound of the formula $PR_3$ wherein R independently represents H or a $C_1$ to $C_{20}$ hydrocarbyl radical with the proviso that any alkenyl substitution be at least 3 carbon atoms removed from the phosphorus atom and at least one R is not H; and (c) at least one acid selected from the group consisting of:

(i) a fluorinated carboxylic acid of the formula R'COOH wherein R' represents a $C_1$ to $C_{10}$ hydrocarbyl radical having at least 1 fluorine (F) atom;

(ii) a dicarboxylic acid of the formula $(R'')_2$—X—(COOH)$_2$ wherein R'' independently represents H or a $C_1$ to $C_{20}$ hydrocarbyl or fluorinated hydrocarbyl radical, and X is a tetravalent C atom or the tetra-substituted benzene radical $C_6H_2$;

(iii) 2-ketobutyric acid; and (iv) glycine.

Exemplary of the phosphine compounds of the formula $PR_3$ are tricyclohexylphosphine, tri-n-butylphosphine, tri-isobutylphosphine, dicyclohexylphenylphosphine, diethylphenylphosphine, dicyclohexylphosphine, tribenzylphosphine, ortho-tolyldiphenylphosphine, and di(ortho-tolyl)phenylphosphine, and mixtures thereof. Preferred is dicyclohexylphosphine.

Examples of fluorinated carboxylic acids of the formula R'COOH for use in the present invention are trifluoracetic acid, heptafluorobutyric acid, difluoroacetic acid, pentafluoropropionic acid, perfluoroadipic acid, and mixtures thereof. Preferred are trifluoroacetic and heptafluorobutyric.

Exemplary dicarboxycyclic acids of the formula $(R'')_2$—C—(COOH)$_2$ are malonic acid, ethylmalonic acid, dimethylmalonic acid, benzylmalonic acid, dimethylmalonic acid, 2,2'-bis(trifluoromethyl)malonic acid, fluorotrifluoromethylmalonic acid, phthalic acid, isophthalic acid, and terephthalic acid, and mixtures thereof. Preferred are benzylmalonic acid and dimethylmalonic acid.

While the order of addition of catalyst precursors is not thought to be critical in the present invention, preferably the inventive composition is made by contacting the catalyst precursors, i.e., a suitable nickel compound, and phosphine compound, each present in a suitable solvent described in this specification, at room temperature for about 15 minutes. Subsequently the acid, present in a solvent, is added.

In the catalyst composition, the molar ratio of the phosphine ligand to the nickel compound can be broadly about 0.01–4.0 to 1, preferably about 0.5–2.5 to 1. The molar ratio of the particular acid used to the nickel compound should generally be about 0.01–10.0 to 1, preferably 0.05–2.0 to 1.

In accordance with another embodiment of the present invention we have discovered that ethylene is efficiently oligomerized by contacting ethylene at a temperature from about 0° C. to about 200° C. with the catalyst composition described in an earlier embodiment of the present invention, said catalyst composition being present in at least one solvent selected from the groups consisting of:

(i) an aromatic hydrocarbon of the formula

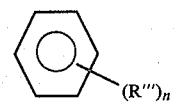

wherein R''' represents a $C_1$ to $C_6$ alkyl radical and n is 0, 1, 2, 3, or 4;

(ii) an alcohol of the formula $(R^{iv})_3COH$ wherein $R^{iv}$ independently represents H or a $C_1$ to $C_{12}$ alkyl, cycloalkyl, aryl, alkaryl, or aralkyl radical with the proviso that at least one $R^{iv}$ is not hydrogen;

(iii) an amide of the formula

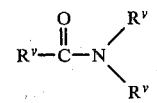

wherein each $R^v$ independently represents H or a $C_1$ to $C_{10}$ alkyl, cycloalkyl, aryl, aralkyl, or alkaryl radical with the proviso that at least one $R^v$ is not H;

(iv) a $C_2$ to $C_{20}$ ether;
(v) a $C_2$ to $C_{20}$ ester;
(vi) a $C_3$ to $C_{20}$ ketone;
(vii) a $C_2$ to $C_{20}$ nitrile; and
(viii) a $C_6$ to $C_{20}$ chlorinated aromatic.

After the inventive catalyst, present in at least one solvent, is prepared as described above, it is contacted with ethylene. The precise method of establishing ethylene/catalyst contact during the reaction is not critical. In one modification, the catalyst system is charged to an autoclave or other similar pressure (vessel) reactor, the ethylene is introduced, and the reaction mixture is maintained with agitation at reaction temperature and pressure for the desired reaction period.

Aromatic hydrocarbon solvents of the formula

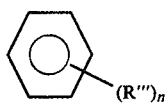

contemplated for use in the present invention include benzene, toluene, xylenes, trimethylbenzenes, ethylbenzenes, cumene and mixtures thereof. Toluene is presently preferred.

Exemplary alcohols of the formula $(R^{iv})_3COH$ include ethanol, 2-butanol, isobutanol, tertiary-butanol, 2-pentanol, 1-hexanol and mixtures thereof. Preferred are 2-pentanol and tertiary butanol because they give high productivity, selectivity and ease of removal and/or recycle.

Exemplary amides of the formula

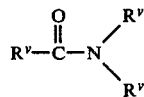

for use in the present invention include N,N-dimethylformamide, N,N-diphenylformamide, acetamide, N,N-dimethylacetamide, N-ethylformamide, N,N-diphenylbenzamide, benzamide and mixtures thereof. Preferred are N,N-diphenylformamide and N,N-dimethylacetamide.

Examples of $C_2$ to $C_{20}$ ethers are dimethyl ether, diethyl ether, dipropyl ether, diphenyl ether, dibutyl ether, ethyl butyl ether, 1,2-dimethoxyethane and mixtures thereof. Preferred are 1,2-dimethoxyethane and diphenyl ether.

Examples of $C_2$ to $C_{20}$ esters include ethyl acetate, propyl acetate, ethyl propionate, methyl acetate, and mixtures thereof. Ethyl acetate is preferred.

Examples of $C_3$ to $C_{20}$ ketones are acetone, methyl ethyl ketone, acetophenone, 2-pentanone, 3-pentanone, 2-hexanone, cyclohexanone and mixtures thereof. Preferred are acetone and methyl ethyl ketone.

Examples of $C_2$ to $C_{20}$ nitriles are acetonitrile, propionitrile, benzonitrile, and mixtures thereof. Preferred is acetonitrile.

Examples of $C_6$ to $C_{20}$ chlorinated aromatics include chlorobenzene, chloroxylenes, dichlorobenzenes, chlorotoluenes, and mixtures thereof. Preferred is chlorobenzene.

Whatever solvent is used, of course, must exist as a liquid at oligomerization reaction conditions.

The weight ratio of the solvent employed to the combination of the nickel compound, phosphine compound and acid components can be broadly $1-10^6$ to 1 with the amount of the solvent used limited only by its cost, the ease of product recovery therefrom, the required reaction vessel size, and other practical considerations. The preferred weight ratio is about 5–10,000 to 1.

Broadly, reaction temperatures vary from about 0° C. to 200° C., preferably from about 20° C. to 125° C.

The reaction pressure is not thought to be critical but typically varies from about 5–5000 psig, preferably from about 200–2000 psig.

The reaction time is broadly from about 1 minute to 18 hours, preferably from about 5 minutes to 5 hours.

The oligomerization products are separated and recovered from the reaction mixture by conventional methods such as fractional distillation, selective extraction, and adsorption.

It is within the scope of this invention to employ a batchwise or continuous reaction system wherein ethylene is passed in a continuous manner into a reaction zone containing the inventive catalyst system while ethylene oligomerization product mixture is concomitantly withdrawn from the reaction mixture.

The following examples further illustrate the present invention.

EXAMPLE I

This example describes the generalized reaction conditions in accordance with which all the runs in Examples II–VI were carried out.

All runs described in Examples II–VI were carried out in a 300 mL stainless steel (316SS) Autoclave Engineers stirred tank reactor. The reactor was first charged with 50 mL of solvent, sealed under nitrogen, then pressured with ethylene and vented to aid oxygen removal. Under a sweep of ethylene, 0.5 g of bis(1,5-cyclooctadiene)nickel(O) (Ni(O)COD) was added, in a minimum volume of solvent (generally toluene). Then, the desired amount of a phosphine compound was added, dissolved in a minimum volume of solvent (generally toluene). This mixture was stirred for about 15 minutes, then the acid component to be employed was added, dissolved in a minimum volume of solvent (generally toluene). The reactor was then charged with ethylene to a predetermined pressure, and reaction allowed to proceed in the range of room temperature to about 80° C., heating or cooling provided as necessary. The reaction pressure employed varied from about 200 to about 1000 psig. The desired pressure was maintained by periodic incremental additions of ethylene with up to about 15 additions per run. When the reaction was complete, the reactor was cooled to below room temperature, the ethylene pressure vented, and the reactor contents purged with nitrogen before opening the vessel.

The resulting product mixture was weighed to determine weight gain and then filtered prior to gas liquid chromatographic (GLC) analysis. A 150′×0.01″ glass or stainless steel capillary column coated with OV-101 was employed for sample analysis. Analysis conditions were 100° C. for two minutes after injection, followed by 32°/min temperature program up to 200° C. final column temperature.

In the following examples, reaction results are reported in terms of catalyst productivity, wt % $C_4$, and the % 1-olefin, % 2-olefin and % branching of the $C_{10}$ fraction. Catalyst productivity is defined as the grams of oligomerized (i.e. $C_4$ and greater) product produced per gram of Ni per hour. Productivity in some cases was calculated based on grams of ethylene reacted and in other cases was determined by comparing final weight of reactor contents with initial weight of reactor contents. The wt % $C_4$ is the wt % of $C_4$ of the total oligomerization product. In most reactions this was calculated from the $C_{10}$ to $C_{16}$ olefin ratios. The accuracy of this method was confirmed by trapping total product in some runs. Catalyst selectivity to α-olefin is measured by analyzing the $C_{10}$ fraction of the oligomerization higher than $C_4$. A selectivity to α-olefin product of about 90% (Runs 5 and 6) is achieved as determined by analysis of the $C_{10}$ product fraction.

EXAMPLE III

A series of runs were carried out in 2-pentanol solvent, with Ni(O)COD, DCHP and a variety of dicarboxylic acids, following the general procedure described above in Example I. Thus, 50 mL of 2-pentanol and reagents as listed in Table II were charged to the reactor. Reaction parameters and results are summarized in Table II.

TABLE II

| | | | | Reaction Parameters | | | | | C-10 fraction, wt % | | |
|---|---|---|---|---|---|---|---|---|---|---|---|
| | Reagents, mmol | | | Time, | Temp, | Press, | | Wt % | | | |
| Run | Acid | | Ni(COD) | DCHP | min. | °C. | psig | Productivity | $C_4$ | 1-olefin | 2-olefin | Branching |
| 1 | None | | 1.82 | 1.87 | 240 | 50 | 850 | | | Trace | | |
| 2 | Oxalic, | 1.3 | 1.93 | 1.92 | 180 | 50 | 800 | | | Trace | | |
| 3 | Adipic, | 1.0 | 2.0 | 1.97 | 165 | 50 | 850 | 20 | | Trace | | |
| | (1) Malonic acid derivatives: | | | | | | | | | | | |
| 4 | Et Malonic, | 1.7 | 1.64 | 1.67 | 150 | 55 | 700 | 340 | 30 | 93 | 5 | 3 |
| 5 | Benzyl Malonic, | 1.6 | 1.67 | 1.67 | 150 | 60 | 700 | 530 | 34 | 90 | 7 | 4 |
| 6 | $Me_2$ Malonic, | 1.7 | 1.78 | 1.82 | 120 | 60 | 700 | 340 | 27 | 95 | 4 | 2 |
| 7 | $Me_2$ Malonic, | 1.9 | 1.89 | 1.87 | 210 | 55 | 700 | 290 | 26 | 95 | 3 | 2 |
| 8 | $Me_2$ Malonic, | 1.7 | 1.67 | 1.67 | 150 | 55 | 700 | 320 | 30 | 95 | 3 | 2 |
| 9 | $Me_2$ Malonic, | 1.9 | 1.93 | 1.92 | 175 | 55 | 700 | 320 | 21 | 95 | 4 | 2 |
| 10 | $Me_2$ Malonic, | 2.0 | 2.07 | 2.07 | 140 | 55 | 700 | 270 | 27 | 94 | 4 | 2 |
| 11 | $Et_2$ Malonic, | 2.0 | 2.00 | 1.97 | 115 | 55 | 700 | 150 | 66 | 91 | 5 | 4 |
| | (2) Aromatic dicarboxylic acids: | | | | | | | | | | | |
| 12 | Terephthalic, | 0.9 | 1.75 | 1.77 | 320 | 55 | 700 | 70 | 26 | 93 | 5 | 2 |
| 13 | Phthalic, | 0.9 | 1.75 | 1.82 | 250 | 35 | 600 | 70 | 62 | 93 | 2 | 5 |
| 14 | Isophthalic, | 1.0 | 2.22 | 2.27 | 230 | 45 | 750 | 60 | 30 | 90 | 8 | 2 | product for 1-olefin, 2-olefin and branched $C_{10}$ olefin. Thus, these numbers represent analysis just of the $C_{10}$ fraction, with no indication of yield of the $C_{10}$ product.

EXAMPLE II

A series of runs were carried out in 2-pentanol as solvent, with bis(1,5-cyclooctadiene)nickel(O) [Ni(O)-COD], dicyclohexylphosphine [DCHP] and a variety of monocarboxylic acids, following the general procedure described above. Thus, 50 mL of 2-pentanol and reagents as listed in Table I were charged to the reactor. Reaction parameters and results are summarized in Table I.

The data demonstrate that dicarboxylic acids such as the malonic acid derivatives studied in runs 4–11 and the aromatic derivatives studied in runs 12–14 are effective catalyst components for the oligomerization of ethylene to α-olefin products compared to the presence of either no acid additive (Run 1) or additives which are not part of the inventive system (Runs 2 and 3). The malonic acid derivatives give high catalyst productivities, with excellent selectivity to α-olefin products. The aromatic diacids, while giving lower catalyst productivities than the malonic acid derivatives, give excellent selectivities to α-olefin products.

TABLE I

| | | | | Reaction Parameters | | | | | C-10 fraction, wt % | | |
|---|---|---|---|---|---|---|---|---|---|---|---|
| | Reagents, mmol | | | Time, | Temp, | Press, | | Wt % | | | |
| Run | Acid | | Ni(COD) | DCHP | min. | °C. | psig | Productivity | $C_4$ | 1-olefin | 2-olefin | Branching |
| 1 | None | | 1.82 | 1.87 | 240 | 50 | 850 | | | Trace | | |
| 2 | $CH_3CO_2H$, | 0.83 | 1.93 | 1.97 | 150 | 50 | 850 | | | Trace | | |
| 3 | $CH_2ClCO_2H$, | 2.0 | 2.04 | 1.92 | 150 | 35 | 650 | 40 | 63 | 55 | 25 | 20 |
| 4 | $CCl_3CO_2H$, | 1.8 | 1.85 | 1.82 | 175 | 50 | 800 | | | Trace | | |
| 5 | $CF_3CO_2H$, | 0.96 | 1.89 | 1.92 | 80 | 55 | 600 | 700 | 42 | 90 | 7 | 4 |
| 6 | Heptafluorobutyric, | 1.9 | 1.85 | 1.87 | 42 | 55 | 700 | 1860 | 50 | 90 | 5 | 5 |

The above data demonstrate that fluorinated carboxylic acids such as trifluoroacetic acid (Run 5) and heptafluorobutyric acid (Run 6) are effective catalyst components for the oligomerization of ethylene to α-olefin products compared to non-fluorinated acids (Runs 1–4). These fluorinated additives give very high catalyst productivities with at least half of the product mix as olefins

EXAMPLE IV

Several runs were carried out in 2-pentanol solvent, with Ni(O)COD, DCHP and a variety of polyfunctional acids, following the general procedure set forth above. Thus, 50 mL of 2-pentanol and reagents as listed in Table III were charged to the reactor. Reaction parameters and results are summarized in Table III.

TABLE III

| Run | Reagents, mmol Acid | | Ni(COD) | DCHP | Reaction Parameters Time, min. | Temp, °C. | Press, psig | Productivity | Wt % C4 | C-10 fraction, wt % 1-olefin | 2-olefin | Branching |
|---|---|---|---|---|---|---|---|---|---|---|---|---|
| 1 | None | | 1.82 | 1.87 | 240 | 50 | 850 | | | Trace | | |
| 2 | 3-hydroxybutyric, | 1.7 | 1.75 | 1.77 | 130 | 55 | 800 | 30 | 56 | 89 | 3 | 8 |
| 3 | 4-acetylbutyric, | 1.9 | 1.93 | 1.87 | 125 | 50 | 750 | 20 | 63 | 98 | 2 | tr |
| 4 | DL-α-hydroxycaproic, | 1.9 | 1.89 | 1.87 | 130 | 50 | 850 | 20 | 70 | 63 | 21 | 16 |
| 5 | 2-Ketobutyric, | 1.9 | 1.85 | 1.87 | 140 | 50 | 760 | 50 | 6 | 95 | 0 | 5 |
| 6 | Glycine, | 1.5 | 1.53 | 1.52 | 120 | 55 | 875 | 130 | 38 | 96 | 3 | 1 |

The data demonstrate that the polyfunctional acids 2-ketobutyric acid (Run 5) and glycine (Run 6) are effective catalyst components for the oligomerization of ethylene to α-olefin products. 2-Ketobutyric acid shows greater than 90% selectivity for oligomers higher than C4, with excellent selectivity to α-olefin product. Essentially no olefin isomerization, as measured by production of α- and β-olefin in the C10 fraction, is observed, while only low levels of branched oligomers are observed. Glycine demonstrates surprisingly high catalyst productivity when compared to the other polyfunctional acids studied. In addition, glycine gives greater than 95% selectivity to α-olefin product, with only low levels of β-olefin and branched olefin observed.

EXAMPLE V

A series of runs were carried out in accordance with the general procedure described above. Thus, 50 mL of toluene, Ni(O)COD, trifluoroacetic acid (TFA) and a variety of phosphines were charged to the reactor. Reaction parameters and results are summarized in Table IV.

TABLE IV

| Run | Phosphine | Ni(COD) | TFA | Time, min. | Temp., °C. | Press, psig | Productivity | Wt % C4 | 1-olefin | 2-olefin | Branching |
|---|---|---|---|---|---|---|---|---|---|---|---|
| 1 | 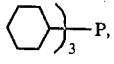 (Cy)₃P | 1.9 | 1.93 | 1.93 | 120 | 50 | 300 | 250 | 18 | 32 | 59 | 9 |
| 2 | (PhCH₂)₃P, | 1.8 | 1.82 | 1.84 | 55 | 50 | 500 | 1480 | 56 | 51 | 22 | 27 |
| 3 | 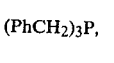 (Cy)₂PH, | 1.7 | 1.64 | 1.67 | 75 | 55 | 500 | 880 | 21 | 69 | 23 | 8 |
| 4 | PhEt₂P, | 1.5 | 1.75 | 1.75 | 110 | 54 | 300 | 360 | 57 | 70 | 11 | 19 |
| 5 | 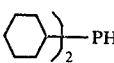 CyPPh₂, | 1.8 | 1.82 | 1.84 | 100 | 50 | 300 | 490 | 63 | 43 | 20 | 37 |
| 6 | 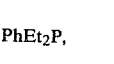 Cy₂PPh, | 1.9 | 1.93 | 1.93 | 90 | 50 | 300 | 720 | 33 | 64 | 26 | 10 |
| 7 | 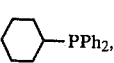 (o-tolyl)PPh₂, | 1.6 | 1.75 | 1.67 | 90 | 50 | 400 | 410 | 51 | 48 | 32 | 20 |
| 8 | 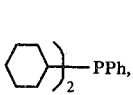 (o-tolyl)₂PPh, | 1.9 | 1.96 | 1.93 | 90 | 50 | 300 | 750 | 50 | 15 | 8 | 77 |

The above data demonstrate that a variety of simple phosphines are effective catalyst components for the oligomerization of ethylene to α-olefin products. High catalyst productivities are achieved in all instances with good selectivities to α-olefin except in Run 8.

EXAMPLE VI

A series of runs were carried out in a variety of solvents, employing 50 mL of total solvent in each run, either as pure solvent or in admixture with toluene. In all runs, Ni(O)COD, DCHP, and TFA were added dissolved in about 10 mL of additional toluene. Amounts of reagents charged, reaction parameters and results are presented in Table V.

TABLE V

| Run | Solvent | Ni(COD) | DCHP | TFA | Time, min. | Temp, °C. | Press, psig | Productivity | Wt % C4 | 1-olefin | 2-olefin | Branching |
|---|---|---|---|---|---|---|---|---|---|---|---|---|
| 1 | Toluene | 1.63 | 1.67 | 1.67 | 75 | 54 | 500 | 880 | 21 | 69 | 23 | 8 |
| 2 | Toluene | 1.82 | 1.77 | 1.75 | 50 | 60 | 700 | 1360 | 23 | 69 | 24 | 7 |
| 3 | 40 mL Toluene | 2.15 | 2.12 | 2.11 | 140 | 47 | 875 | 10 | | | trace | |

TABLE V-continued

| Run | Solvent | Reagents, mmol | | | Reaction Parameters | | | Productivity | Wt % C$_4$ | C-10 fraction, wt % | | |
|---|---|---|---|---|---|---|---|---|---|---|---|---|
| | | Ni(COD) | DCHP | TFA | Time, min. | Temp, °C. | Press, psig | | | 1-olefin | 2-olefin | Branching |
| 4 | 10 g formamide 40 mL Toluene/ 10 g HMPA | 1.71 | 1.67 | 1.67 | 140 | 55 | 700 | 90 | 41 | 67 | 25 | 8 |
| 5 | Formamide | 1.78 | 1.72 | 1.75 | 150 | 50 | 700 | 10 | | | trace | |
| 6 | Methanol | 2.00 | 2.00 | 2.00 | 180 | 63 | 400 | 260 | 80 | 43 | 22 | 35 |
| 7 | 40 mL Toluene/ morpholine | 1.75 | 1.77 | 1.75 | 180 | 54 | 800 | | | trace | | |
| 8 | 40 mL Toluene/ 10 mL N,N—DMF | 1.74 | 1.82 | 1.75 | 190 | 52 | 700 | 260 | 34 | 84 | 10 | 6 |
| 9 | 40 mL Toluene/ 10 g diphenylformamide | 1.67 | 1.72 | 1.67 | 60 | 55 | 700 | 1390 | 30 | 74 | 20 | 6 |
| 10 | 40 mL Toluene/ 10 g acetamide | 1.64 | 1.72 | 1.67 | 120 | 54 | 700 | 380 | 36 | 63 | 32 | 6 |
| 11 | 40 mL Toluene/ 10 mL dimethylacetamide | 1.89 | 1.92 | 1.93 | 110 | 55 | 700 | 540 | 29 | 79 | 14 | 7 |
| 12 | 40 mL Toluene/ 10 g phthalimide | 1.93 | 1.97 | 1.93 | 110 | 58 | 700 | 900 | 27 | 70 | 23 | 8 |
| 13 | N,N—DMF | 2.11 | 2.17 | 2.11 | 175 | 54 | 700 | 140 | 60 | 86 | 7 | 7 |
| 14 | N,N—Dimethylacetamide | 1.67 | 1.67 | 1.67 | 170 | 55 | 700 | 200 | 50 | 78 | 12 | 10 |
| 15 | EtOH | 1.89 | 1.82 | 1.93 | 100 | 53 | 500 | 290 | 72 | 77 | 5 | 18 |
| 16 | s-BuOH | 2.00 | 2.02 | 2.02 | 130 | 55 | 500 | 210 | 54 | 88 | 6 | 7 |
| 17 | i-BuOH | 1.96 | 2.02 | 1.93 | 210 | 66 | 500 | 260 | 70 | 67 | 17 | 16 |
| 18 | t-BuOH | 1.89 | 1.97 | 1.93 | 95 | 57 | 500 | 520 | 36 | 89 | 6 | 6 |
| 19 | 2-C$_5$OH | 1.89 | 1.92 | 0.96 | 80 | 55 | 600 | 700 | 43 | 90 | 7 | 4 |
| 20 | 40 mL Toluene/ 10 mL Ph$_2$O | 1.78 | 1.87 | 1.75 | 100 | 60 | 700 | 770 | 41 | 78 | 12 | 10 |
| 21 | 40 mL Toluene/ 10 mL DME* | 1.85 | 1.82 | 1.84 | 75 | 55 | 700 | 1130 | 23 | 71 | 22 | 7 |
| 22 | 40 mL Toluene/ 10 mL CH$_3$CN | 2.00 | 2.07 | 2.01 | 100 | 57 | 700 | 770 | 58 | 73 | 19 | 8 |
| 23 | 40 mL Toluene/ 10 mL acetone | 1.85 | 1.92 | 1.84 | 45 | 55 | 700 | 1400 | 28 | 76 | 17 | 7 |
| 24 | 40 mL Toluene/ 10 mL MEK | 1.89 | 1.82 | 1.93 | 50 | 55 | 700 | 2140 | 32 | 75 | 17 | 8 |
| 25 | 40 mL Toluene/ 10 mL EtOAc | 1.82 | 1.77 | 1.84 | 50 | 55 | 700 | 1720 | 32 | 73 | 18 | 9 |
| 26 | 40 mL Toluene/ 10 mL PhCl | 1.75 | 1.82 | 1.75 | 50 | 53 | 700 | 2550 | 29 | 74 | 18 | 9 |

*1,2-dimethoxyethane

The results of Runs 1, 2, and 8–26 demonstrate that a variety of solvents, either alone or in admixture with a co-solvent such as toluene, are effective solvents for the oligomerization of ethylene to α-olefin products compared to solvents or admixtures which are not effective in the inventive system (Runs 3–7).

Catalyst productivities as high as 2500 g of oligomer/g Ni/hr are achieved (see run 26; PhCl solvent) and high selectivities to α-olefin products are possible using such solvents as t-butanol and 2-pentanol (see runs 18 and 19). In addition, by appropriate choice of solvent, varying levels of C$_4$ versus higher oligomers can be obtained—compare Runs 15 (72%) and 21 (23%), for example.

Reasonable variations and modifications are possible within the scope of the foregoing.

We claim:

1. A composition consisting essentially of:
   (a) at least one nickel compound selected from the group consisting of:
   bis(1,5-cyclooctadiene)nickel(O),
   bis(tricyclohexylphosphine)nickel(O),
   nickel tetracarbonyl,
   (cyclododecatriene)nickel, and
   bis(ethylene)(dicyclohexylphosphine)nickel;
   (b) a phosphine compound of the formula PR$_3$ wherein R represents H or a C$_1$ to C$_{20}$ hydrocarbyl radical with the proviso that any alkenyl substitution be at least 3 carbon atoms removed from the phosphorus atom and at least one R is not H; and
   (c) an acid selected from the group consisting of (i) a fluorinated carboxylic acid of the formula R'COOH wherein R' represents a C$_1$ to C$_{10}$ hydrocarbyl radical having at least 1 fluorine (F) atom, (ii) a dicarboxyclic acid of the formula (R")$_2$—X—(COOH)$_2$ wherein R" independently represents H or a C$_1$ to C$_{20}$ hydrocarbyl or fluorinated hydrocarbyl radical and X is a tetravalent C atom or the tetra-substituted benzene radical C$_6$H$_2$, (iii) 2-ketobutyric acid and (iv) glycine, such that the molar ratio of (b) to (a) is about 0.01–4.0 to 1 and the molar ratio of (c) to (a) is about 0.01–10.0 to 1.

2. A composition according to claim 1 wherein (a) is bis(1,5-cyclooctadiene) nickel(O).

3. A composition according to claim 1 wherein (b) is one selected from the group consisting of tricyclohexylphosphine, triisobutylphosphine, tri-n-butylphosphine, dicyclohexylphenylphosphine, diethylphenylphosphine, dicyclohexylphosphine, tribenzylphosphine, ortho-tolyldiphenylphosphine, and di(ortho-tolyl)phenylphosphine.

4. A composition according to claim 3 wherein (b) is dicyclohexylphosphine.

5. A composition according to claim 2 wherein (b) is dicyclohexylphosphine.

6. A composition according to claim 5 wherein (c) is trifluoroacetic acid.

7. a composition according to claim 5 wherein (c) is heptafluorobutyric acid.

8. A composition according to claim 5 wherein (c) is 2-ketobutyric acid.

9. A composition according to claim 5 wherein (c) is glycine.

10. A composition according to claim 5 wherein (c) is one selected from the group consisting of malonic acid, ethylmalonic acid, dimethylmalonic acid, benzylmalonic acid, and diethylmalonic acid.

11. A composition according to claim 10 wherein (c) is dimethylmalonic acid.

12. A composition according to claim 1 wherein the molar ratio of (b) to (a) is about 0.5–2.5 to 1 and the molar ratio of (c) to (a) is about 0.01–10.0 to 1.

* * * * *